United States Patent [19]

Elger et al.

[11] Patent Number: 4,834,985
[45] Date of Patent: May 30, 1989

[54] CONTROLLED RELEASE PHARMACEUTICAL COMPOSITION

[75] Inventors: Gordon Elger, Huntingdon; Stewart T. Leslie, Cambridge; Sandra T. A. Malkowska, Landbeach, all of United Kingdom; Ronald B. Miller, Basel, Switzerland; Philip J. Neale, Harston, United Kingdom

[73] Assignee: Euroceltique S.A., Luxembourg

[21] Appl. No.: 52,585

[22] Filed: May 19, 1987

[30] Foreign Application Priority Data

Jun. 5, 1986 [GB] United Kingdom ............... 8613688

[51] Int. Cl.$^4$ .............................................. A61K 9/14
[52] U.S. Cl. .................................... 424/488; 424/457; 424/458; 424/468; 424/469; 424/484; 424/490; 424/494; 424/499; 424/502
[58] Field of Search ............... 424/485, 498, 502, 484, 424/488, 457, 458, 468, 469, 490, 494, 499

[56] References Cited

U.S. PATENT DOCUMENTS

| | | | |
|---|---|---|---|
| 2,921,883 | 1/1960 | Reese et al. ................. | 424/498 X |
| 3,082,154 | 3/1963 | Allan ............................ | 424/498 |
| 3,084,294 | 3/1963 | Shepard ....................... | 424/498 |
| 3,147,187 | 9/1964 | Playfair ........................ | 424/502 |
| 3,492,397 | 1/1970 | Peters et al. ................. | 424/498 X |
| 3,922,339 | 11/1975 | Shear .......................... | 424/498 |
| 4,722,815 | 2/1988 | Shibanai ...................... | 424/502 |

FOREIGN PATENT DOCUMENTS

| | | | |
|---|---|---|---|
| D. 635283 | 1/1962 | Canada ........................ | 424/498 |
| 1044572 | 10/1966 | United Kingdom .......... | 424/498 |

Primary Examiner—Thurman K. Page
Attorney, Agent, or Firm—Steinberg & Raskin

[57] ABSTRACT

A solid, controlled release, pharmaceutical composition comprising an active ingredient incorporated in a matrix comprising a first substance selected from a water soluble polydextrose and a water soluble cyclodextrin and a second substance selected from a $C_{12}-C_{36}$ fatty alcohol and a polyalkylene glycol.

Preferably the first substance is a cyclodextrin, especially a beta-cyclodextrin, while the second substance is a $C_{14}-C_{22}$ fatty alcohol, especially stearyl alcohol, cetyl alcohol, cetostearyl alcohol or myristyl alcohol. The matrix may also contain a cellulose ether, especially a hydroxyalkylcellulose or a carboxyalkylcellulose.

20 Claims, 3 Drawing Sheets

CONTROLLED RELEASE PHARMACEUTICAL COMPOSITION

The present invention relates to a solid controlled release pharmaceutical composition.

A "controlled release pharmaceutical composition" is one that achieves slow release of a drug over an extended period of time and extends the duration of drug action over that achieved by conventional delivery. Preferably such a composition maintains drug level in the blood or target tissue within the therapeutic range for 8 hours or more.

A controlled (sustained) release pharmaceutical composition containing an active ingredient has many advantages over a normal release form of the same ingredient. These include a reduction of the frequency of administration, a decrease in side effects and the maintenance of effective concentrations of the active material in the blood.

It is an object of the present invention to provide a controlled release pharmaceutical composition that exercises particularly good control over the release of the active ingredient.

Other objects and advantages of the present invention will become apparent from the following detailed description thereof.

According to the present invention, therefore, there is provided a solid, controlled release, pharmaceutical composition comprising an active ingredient incorporated in a matrix comprising a first substance selected from a water-soluble polydextrose and a water-soluble cyclodextrin and a second substance selected from a $C_{12}$–$C_{36}$ fatty alcohol and a polyalkylene glycol.

In the present specification, "water soluble" means that the polydextrose or cyclodextrin dissolves to a level of at least 1% (w/w) in water at 25° C.

Although the polydextrose employed in the present composition may have an average molecular weight of between about 360 and $10^6$, preferably the polydextrose has a number average molecular weight between 1000 and 12000. Polydextrose is a non-nutritive polysaccharide, prepared by the condensation polymerisation of saccharides in the presence of polycarboxylic acid catalysts, under reduced pressure.

Polydextrose is described in U.S. Pat. Nos. 3,766,105 and 3,786,794 (the contents of which documents are incorporated herein by reference) and is available from Pfizer Inc., New York. Commercially available polydextrose polymer is generally a low molecular weight, water-soluble, randomly bonded polymer of glucose containing minor amounts of sorbitol end groups and citric acid residues attached to the polymer by mono- and di-ester bonds. The number average molecular weight of this commercially available material is 1500, ranging from about 360 to about 20,000.

In the present specification, "cyclodextrin" incorporates both the naturally occurring clathrates obtained from the action of *Bacillus macerans* amylase on starch to form homogeneous cyclic alpha (1-4) linked D-glucopyranose units (ie. alpha, beta- and gamma-cyclodextrin) but also the methylated derivatives of these natural products, especially of beta-cyclodextrin (eg. heptakis(2,6-di-O-methyl)-beta-cyclodextrin and heptakis(2,3,6-tri-O-methyl)-beta-cyclodextrin.

In a preferred embodiment of the present composition the cyclodextrin (or methylated derivative) is a beta-cyclodextrin.

The amount of polydextrose and/or cyclodextrin present in the composition of this invention will be determined by a number of factors, including the active ingredient to be administered and the rate of drug release required. Preferably, however, the composition will contain between 1% and 80% (w/w), especially between 1% and 50% (w/w) of polydextrose and/or cyclodextrin, most especially between 2% and 40% (w/w) of polydextrose and/or cyclodextrin.

The $C_{12}$–$C_{36}$ fatty alcohol may be any digestible, long chain alcohol. Preferably, it has a melting point between 25° and 95° C. In a particularly preferred embodiment of this invention, the alcohol is a $C_{14}$–$C_{22}$ fatty alcohol such as stearyl alcohol, myristyl alcohol, cetyl alcohol and, which is preferred, cetostearyl alcohol.

The polyalkylene glycol may be, for example, polypropylene glycol or, which is preferred, polyethylene glycol. In a particularly preferred embodiment of the present invention the second substance in the controlled release matrix is a $C_{12}$–$C_{36}$ fatty alcohol, especially a $C_{14}$–$C_{22}$ fatty alcohol.

In addition to the polydextrose, cyclodextrin and alcohol/glycol, the present composition may also include further ingredients which can contribute to the control of the active ingredient's release and are compatible with polydextrose, cyclodextrin, fatty alcohol and polyalkylene glycol.

Of these polymers, the cellulose ethers, especially hydroxyalkylcelluloses and carboxyalkylcelluloses, most especially hydroxyethylcellulose, hydroxypropylcellulose, hydroxypropylmethylcellulose and sodium carboxymethyl cellulose, are preferred.

In preferred compositions according to this invention the ratio of polydextrose/cyclodextrin/hydrophilic and/or hydrophobic polymer to fatty alcohol/glycol is between 6 to 1 and 1 to 6, especially between 4 to 1 and 1 to 4.

When the polydextrose and/or cyclodextrin is combined with the $C_{12}$–$C_{36}$ fatty alcohol and/or polyalkylene glycol, the matrix itself is novel. Thus, in another aspect of the present invention, there is provided a preparation for use in the production of a solid, controlled release pharmaceutical composition comprising a matrix of a first substance selected from a water-soluble polydextrose and a water-soluble cyclodextrin and a second substance selected from a $C_{12}$–$C_{36}$, especially $C_{14}$–$C_{22}$, fatty alcohol and a polyalkylene glycol. Optionally the matrix may also contain at least one of a hydroxyalkyl cellulose and a carboxyalkyl cellulose. Preferably the ratio of polydextrose/cyclodextrin/cellulose to fatty alcohol/glycol is between 6 to 1 and 1 to 6, especially between 4 to 1 and 1 to 4.

In addition to the above materials, the present controlled release composition may also contain excipients, such as binders, disintegrating agents, colours, flavours, preservatives, stabilisers, glidants and lubricants, the use of which will be well known to those skilled in the pharmaceutical art.

Although the present controlled release composition may be in any solid dosage form, for example, a suppository or a pessary, it is preferably adapted for oral administration. In the present specification "oral administration" incorporates buccal and sublingual administration. Thus, the preferred oral dosage forms include tablets, buccal tablets, sublingual tablets, lozenges, capsules containing, for example, granules or pellets, and dragees.

Any active ingredient that may be administered by the oral, buccal, sublingual, rectal or vaginal routes may be employed in the controlled release composition of this invention. Those medicaments having a biological half-life below about 8 hours, however, are particularly suitable for incorporation in the present composition.

Examples of active ingredients that may advantageously be incorporated in the present composition are, (1) Anti-allergic drugs, such as cyclizine, dimethindene maleate and triprolidine hydrochloride,
(2) Anti-diabetic drugs, such as chlorpropamide, glibenclamide, metformin and tolbutamide,
(3) Hormones,
(4) Antiarrhythmic agents, such as disopyramide, procainamide, propranolol and quinidine,
(5) Anti-inflammatory agents, such as aspirin, diclofenac sodium, flurbiprofen, ibuprofen, indomethacin, ketoprofen, naproxen and phenylbutazone,
(6) Antiemetic drugs, suc as metoclopramide,
(7) Diuretics, such as amiloride, bendrofluazide, bumetanide, cyclopenthiazide, ethacrynic acid, frusemide, hydrochlorothiazide, triampterene, chlorthalidone and spironolactone,
(8) Anti-anginal agents, such as nitroglycerin, isosorbide dinitrate pentaerythritol tetranitrate, verapamil and diltiazem.
(9) Vasodilators, such as nifedipine, naftidrofuryl oxalate, and nicardipine,
(10) Antihypertensive agents, such as clonidine, indoramin, guanethidine, methyldopa, oxprenolol, captopril, hydralazine and propranolol,
(11) Bronchodilators, such as salbutamol, isoprenaline and terbutaline,
(12) CNS stimulants, such as caffeine and amphetamine,
(13) Anti-histamines, such as clemastine fumarate, mepyramine, chlorpheniramine, brompheniramine, diphenhydramine.
(14) Analgesic agents, such as morphine, codeine, phenazocine, dihydrocodeine, hydromorphone, meptazinol, phenacetin, pethidine, paracetamol, oxycodone, diamorphine, nalbuphine, buprenorphine, and mefenamic acid,
(15) Vitamins, such as Vitamin B1, Vitamin B2, Vitamin B6, Vitamin C and Vitamin E,
(16) Antidepressants, such as lofepramine, amitriptyline, doxepin, maprotiline, imipramine, desipramine and mianserin,
(17) Tranquilisers, such as chlordiazepoxide and diazepam,
(18) Hematinic agents, such as ferrous fumarate,
(19) Respiratory stimulants, such as nikethamide,
(20) Antibacterial agents, such as polymyxin, streptomycin, sulphonamides, penicillins, erythromycin, cephalosporins, nalidixic acid, tetracyclines, hexamine salts, gentamicin and nitrofurantoin,
(21) Hypnotic agents such as barbiturates, dichloral phenazone, nitrazepam and temazepam,
(22) Antiviral agents, such as idoxuridine,
(23) Vasoconstrictors, such as angiotensin amide, dihydroergotamine, and ergotamine,
(24) Topical anaesthetics, such as benzocaine,
(25) Anticholinergic agents, such as scopolamine, atropine and propantheline,
(26) Adrenergic drugs, such as phenylephrine hydrochloride, phenylpropanolamine hydrochloride and pseudoephedrine,
(27) Anthelmintic agents, such as diethylcarbamazine,
(28) Corticosteroids, such as dexamethasone, prednisone, prednisolone and triamcinolone acetonide,
(29) Inorganic drugs, such as lithium carbonate, potassium chloride and lithium sulphate,
(30) Antacids, such as aluminium trisilicate and aluminium hydroxide,
(31) Antiulcer agents, such as cimetidine and ranitidine,
(32) Cofactors, such as nicotinic acid,
(33) Antipsychotic agents, such as thioridazine, trifluoperazine, fluphenazine and haloperidol,
(34) Laxatives, such as bisacodyl and magnesium hydroxide,
(35) Antiperistaltic agents, such as diphenoxylate,
(36) Anticoagulant agents, such as warfarin,
(37) Haemostatic agents, such as epsilon-aminocaproic acid,
(38) Antinauseant agents, such as metoclopramide, pyridoxine and prochlorperazine,
(39) Anticonvulsant agents, such as sodium valproate and phenytoin sodium,
(40) Neuromuscular drugs, such as dantrolene sodium,
(41) Hypoglycaemic agents, such as chlorpropramide, glucagon and tolbutamide,
(42) Thyroid drugs, such as thyroxine, triiodothyronine and propylthiouracil,
(43) Uterine relaxant, such as ritodrine,
(44) Appetite suppressants, such as phentermine, diethylpropion HCl and fenfluramine HCl,
(45) Erythropoietic substances, such as folic acid, calcium gluconate, and ferrous sulphate,
(46) Expectorants, such as carbocisteine and, guiaphenesin,
(47) Cough suppressants, such as noscapine, dextromethorphan and oxycodone,
(48) Antiuricemic drugs, such as allopurinol, probenecid and sulphinpyrazone, Preferably the active ingredient is a water-insoluble drug. In the present specification, a water insoluble drug is a drug that dissolves in water (pH 5) at 20° C. to a concentration of less than 1.0 mgml$^{-1}$, preferably less than 0.5 mgml$^{-1}$.

According to another feature of the present invention, the solid, controlled release, pharmaceutical composition is prepared by mixing an active ingredient with a first substance selected from a water soluble polydextrose and a water soluble cyclodextrin and a second substance selected from a $C_{12}$–$C_{36}$ fatty alcohol and a polyalkylene glycol, optionally in the presence of one or more of the following excipients, a hydrophilic or hydrophobic polymer, a binder, a disintegrating agent, a colour, a flavour, a preservative, a stabiliser, a glidant and a lubricant. Preferably the alcohol is a $C_{14}$–$C_{22}$ fatty alcohol.

In a particularly preferred embodiment of this feature of the invention a solid, controlled release, pharmaceutical composition, in unit dosage form and for oral administration (as hereinbefore defined), is prepared by granulating an active ingredient with a first substance selected from a water soluble polydextrose andd a water soluble cyclodextrin and, optionally, mixing with one or more of the following excipients, a hydrophilic or hydrophobic polymer (other than polydextrose), a binder, a disintegrating agent, a colour, a flavour, a preservative, a stabiliser, a glidant or a lubricant, to form granules, mixing the granules formed with a second substance selected from a $C_{12}$–$C_{36}$ fatty alcohol and a polyalkylene glycol and compressing the granules to give an oral, solid, unit dosage form containing a predetermined, therapeutically active, quantity of the active ingredient. Preferably the alcohol is a $C_{14}$–$C_{22}$ fatty alcohol.

Depending on the particular case, the method of preparation of the granules may involve for example wet granulation or direct compression.

Once the oral, solid unit dosage form has been prepared it may, if desired, be coated, for example with a gasto-resistant coating.

In a further, particularly preferred embodiment of this feature of the invention a solid, controlled release, pharmaceutical composition in the form of a capsule is prepared by pelletising, spheronising or granulating an active ingredient with a first substance selected from a water soluble polydextrose and a water soluble cyclodextrin and a second substance selected from a $C_{12}$–$C_{36}$, especially $C_{14}$–$C_{22}$, fatty alcohol and a polyalkylene glycol and, optionally, one or more of the optional ingredients employed in the preparation of the oral, unit dosage form above, to form pellets, spheroids or granules and encapsulating the pellets, spheroids or granules to give a capsule containing a predetermined, therapeutically active, quantity of the active ingredient.

Prior to filling the capsule with the pellets, the spheroids or the granules, the pellets/spheroids/granules may be coated, for example with a gastro-resistant coating.

According to another feature of the present invention, there is provided a process for the preparation of a matrix for admixture with an active ingredient to form a controlled release pharmaceutical composition comprising mixing a first substance selected from a water soluble polydextrose and a water soluble cyclodextrin with a second substance selected from a $C_{12}$–$C_{36}$ especially a $C_{14}$–$C_{22}$, fatty alcohol and a polyalkylene glycol, especially polyethylene glycol to form a controlled release matrix.

Once the matrix has been granulated it can then be mixed with a predetermined amount of the active ingredient and, optionally compressed, to give a controlled release pharmaceutical composition according to the invention.

Predetermined release patterns of unusually reliable and constant characteristics can be secured using the present composition. This is often very important medically, especially when treating patients having coronary diseases, such as angina pectoris, or related problems, such as circulatory disorders or abnormal blood pressure, or when treating psychotropic disorders, such as manic depression or schizophrenia or when treating bronchial disorders or moderate to severe pain. The present composition may also be extremely useful in the treatment of ulcerated tissues or mucous lesions and other conditions which arise from local hyperacidity or metabolic dysfunction in the physiological system. The present composition is therefore extremely versatile and adaptable giving a wide range of application and end use.

The present solid, controlled release, pharmaceutical composition, together with methods for its preparation will now be described by way of example only, with particular reference to the Figures.

EXAMPLE 1 (COMPARATIVE)

Anhydrous theophylline (40 gm) was wet granulated with hydroxyethylcellulose (2.5 gm; Natrosol 250HX, Trade Mark) and the granules were sieved through a 16 mesh screen. The granules were then dried in a FBD at 60° C.

To the warmed theophylline containing granules was added a molten mixture of polyethylene glycol PEG 6000 (5.0 gm) and cetostearyl alcohol (4.0 gm). This mixture was allowed to air cool and then passed through a 16 mesh screen.

Talc (1.0 gm) and magnesium stearate (1.0 gm) were then mixed with the granules. The granules were compressed to give 100 tablets each containing,

|  | mg/tablet |
| --- | --- |
| Theophylline anhydrous | 400 |
| Hydroxyethylcellulose | 25 |
| PEG 6000 | 50 |
| Cetostearyl alcohol | 40 |
| Talc | 10 |
| Magnesium stearate | 10 |

EXAMPLE 2

The procedure of Example 1 was followed except that polydextrose replaced the hydroxyethylcellulose. This gave 100 tablets, each containing

|  | mg/tablet |
| --- | --- |
| Theophylline anhydrous | 400 |
| Polydextrose | 25 |
| PEG 6000 | 50 |
| Cetostearyl alcohol | 40 |
| Talc | 10 |
| Magnesium stearate | 10 |

Figure 1:
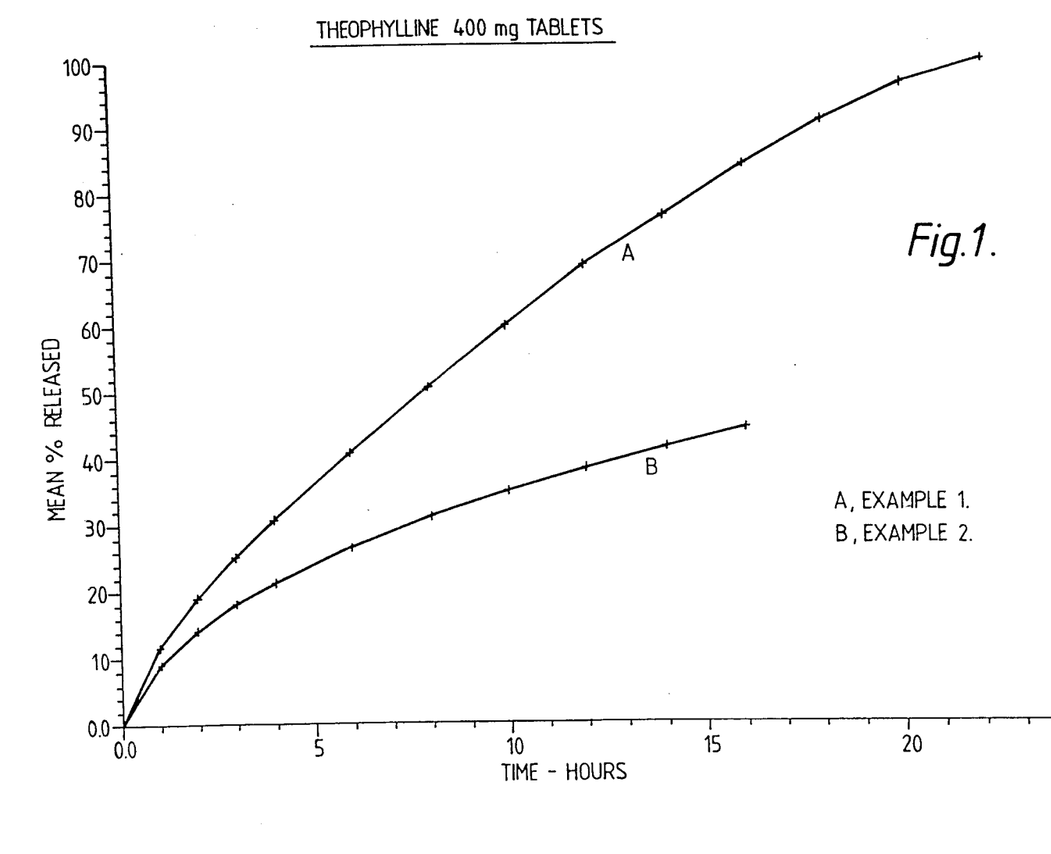
FIG. 1 compares the release rates of two theophylline controlled release formulations, one containing hydroxyethylcellulose and cetostearyl alcohol, the other polydextrose and cetostearyl alcohol, FIG. 2 compares the release rates of two pyridoxine hydrochloride controlled release formulations, one containing hydroxyethylcellulose and cetostearyl alcohol, the other polydextrose and cetostearyl alcohol, and FIG. 3 compares the release rates of two metoclopramide hydrochloride controlled release formulations, one containing hydroxyethylcellulose and cetostearyl alcohol, the other polydextrose and cetostearyl alcohol.

A comparison of the release rates of theophylline from tablets prepared as described in Examples 1 and 2 is shown in FIG. 1. The dissolution rates were measured by the USP Paddle Method at 100 rpm in 900 ml of aqueous buffer (pH 6.5).

EXAMPLE 3 (COMPARATIVE)

Pyridoxine hydrochloride (10 gm) and hydrogenated castor oil (1.5 gm) were granulated with hydroxyethylcellulose (2.0 gm, Natrosol 250HX) and the granules were sieved through a 16 mesh screen and dried in a FBD at 60° C.

To the pyridoxine hydrochloride containing granules, molten cetostearyl alcohol (3.5 gm) was added. This mixture was allowed to air cool and then passed through a 16 mesh screen.

Talc (0.3 gm) and magnesium stearate (0.1 gm) were mixed with the granules. This mixture was compressed to give 100 tablets each containing,

|                        | mg/tablet |
|------------------------|-----------|
| Pyridoxine HCl         | 100       |
| Hydroxyethylcellulose  | 20        |
| Hydrogenated castor oil| 15        |
| Cetostearyl alcohol    | 35        |
| Talc                   | 3         |
| Magnesium stearate     | 1         |

EXAMPLE 4

The procedure of Example 3 was followed except that polydextrose replaced the hydroxyethylcellulose. This gave 100 tablets each containing.

|                        | mg/tablet |
|------------------------|-----------|
| Pyridoxine HCl         | 100       |
| Polydextrose           | 20        |
| Hydrogenated castor oil| 15        |
| Cetostearyl alcohol    | 35        |
| Talc                   | 3         |
| Magnesium stearate     | 1         |

Figure 2:
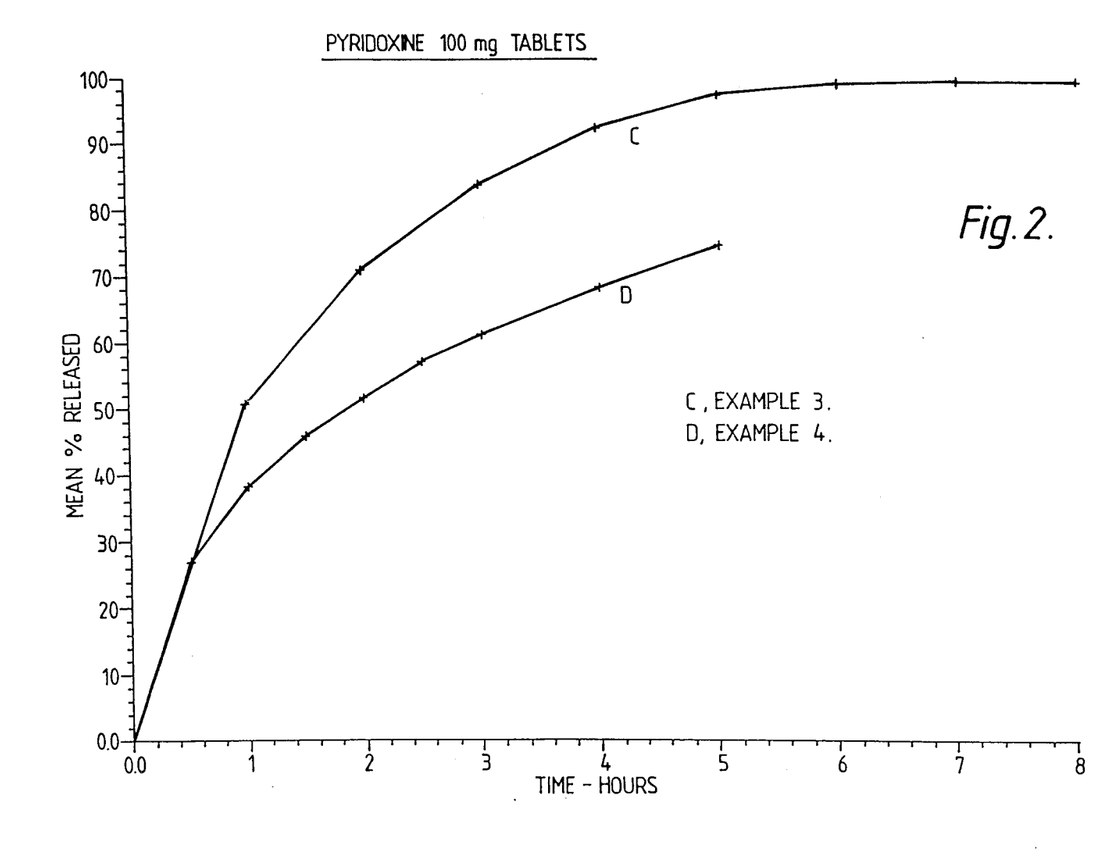

A comparison of the release rates of pyridoxine HCl from tablets prepared as described in Examples 3 and 4 is shown in FIG. 2. The dissolution rates were measured by the USP Paddle Method at 100 rpm in 900 ml of aqueous buffer (pH 6.5).

EXAMPLE 5 (COMPARATIVE)

Metoclopramide HCl (3 gm) was wet granulated with anhydrous lactose (17 gm) and hydroxyethylcellulose (2 gm; Natrosol 250HX) and the granules were sieved through a 16 mesh screen. The granules were then dried in an FBD at 60° C.

To the warmed metoclopramide containing granules was added molten cetostearyl alcohol (7 gm). The mixture was allowed to air cool and then passed through a 16 mesh screen.

Talc (0.6 gm) and magnesium stearate (0.4 gm) were mixed with the granules. The granules were then compressed to give 100 tablets each containing,

|                        | mg/tablet |
|------------------------|-----------|
| Metoclopramide HCl     | 30        |
| Anhydrous lactose      | 170       |
| Hydroxyethylcellulose  | 20        |
| Cetostearyl alcohol    | 70        |
| Talc                   | 6         |
| Magnesium stearate     | 4         |

EXAMPLE 6

Anhydrous lactose (17 gm) and polydextrose (2 gm) were dry mixed. Molten cetostearyl alcohol (7 gm) was added to the dry mixed powders. The mixture was allowed to cool and then passed through a 16 mesh screen.

Metoclopramide HCl (3 gm), talc (6 gm) and magnesium stearate (4 gm) were then mixed with the polydextrose/wax granules and compressed to give 100 tablets each containing,

|                    | mg/tablet |
|--------------------|-----------|
| Metoclopramide HCl | 30        |
| Anhydrous lactose  | 170       |

-continued

|                    | mg/tablet |
|--------------------|-----------|
| Polydextrose       | 20        |
| Cetostearyl alcohol| 70        |
| Talc               | 6         |
| Magnesium stearate | 4         |

Figure 3:
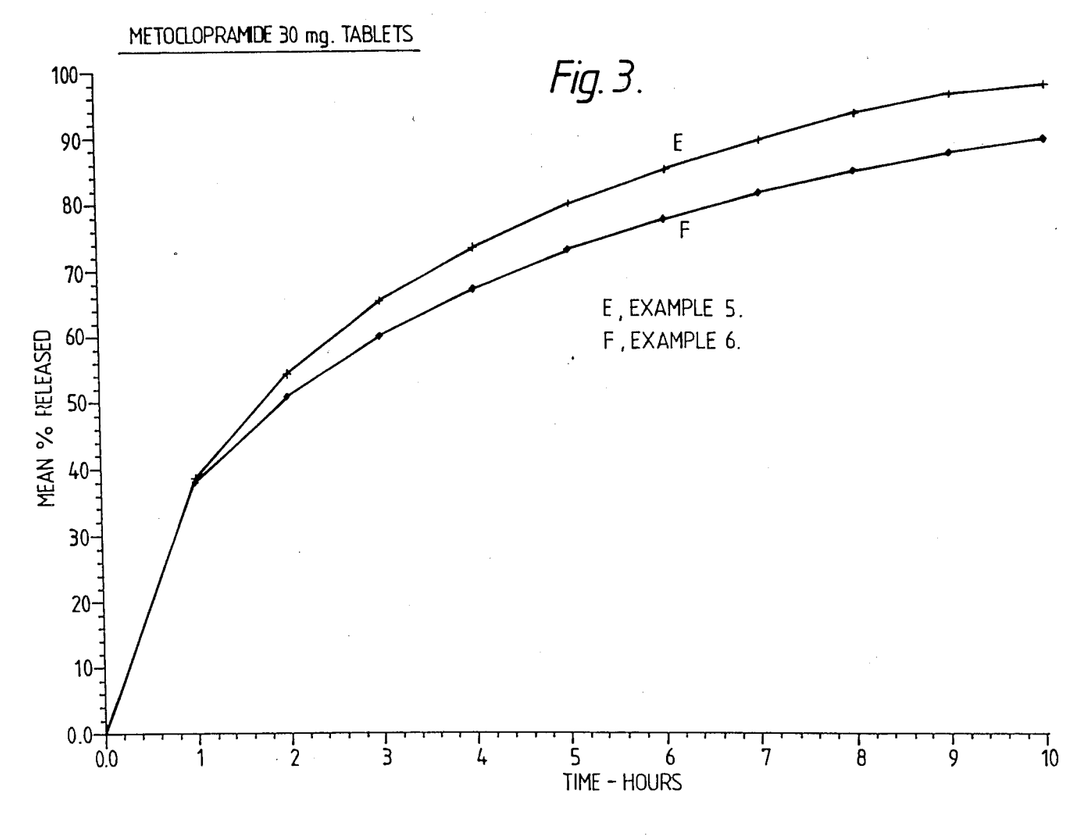

A comparison of the release rates of metoclopramide HCl from tablets prepared as described in Examples 5 and 6 is shown in FIG. 3. The dissolution rates were measured by the USP Paddle Method at 100 rpm in 900 ml of aqueous buffer (pH 6.5).

EXAMPLE 7

Anhydrous theophylline (40 gm) was wet granulated with polydextrose (21.8 gm) and the granules were sieved through a 16 mesh screen. The granules were dried in a FBD at 60° C.

To the warmed theophylline containing granules was added a molten mixture of polyethylene glycol 6000 (2.9 gm), polyethylene glycol 1000 (1.45 gm) and cetostearyl alcohol (2.9 gm). This mixture was allowed to air cool and then passed through a 16 mesh screen.

Talc (1.0 gm) and magnesium stearate (0.45 gm) were then mixed with the granules. The granules were compressed to give 100 tablets each containing.

|                       | mg/tablet |
|-----------------------|-----------|
| Theophylline anhydrous| 400       |
| Polydextrose          | 218       |
| PEG 6000              | 29        |
| PEG 1000              | 14.5      |
| Cetostearyl alcohol   | 29        |
| Talc                  | 10        |
| Magnesium stearate    | 4.5       |

The dissolution rate in-vitro of those tablets were measured by the USP Paddle Method at 100 rpm in 900 ml of aqueous buffer (pH 6.5). Results are shown in Table 1.

TABLE 1

| In vitro Dissolution of Theophylline Tablets | |
|---|---|
| Time (Hours) | % (by wt) Released |
| 2  | 21.7 |
| 4  | 33.7 |
| 6  | 42.3 |
| 8  | 49.0 |
| 10 | 54.3 |
| 12 | 58.3 |
| 14 | 62.0 |
| 16 | 65.0 |
| 18 | 67.8 |

EXAMPLE 8

Naproxen (50 gm), dicalcium phosphate (16.4 g), lactose (2.5 gm), polydextrose (2.0 gm) and hydroxypropylmethylcellulose (2.0 gm) were wet granulated and the granules were sieved through a 16 mesh screen. The granules were then dried in a FBD at 50° C. Talc (1.35 gm) and magnesium stearate (0.75 gm) were then added and mixed with the granules. The granules were then compressed to give 100 tablets containing;

|                              | mg/tablet |
|------------------------------|-----------|
| Naproxen                     | 500       |
| Dicalcium phosphate, anhydrous | 164     |

| -continued | |
|---|---|
| | mg/tablet |
| Lactose monohydrate | 25 |
| Polydextrose | 20 |
| Hydroxypropylmethylcellulose | 20 |
| Talc | 13.5 |
| Magnesium stearate | 7.5 |

The dissolution rate in-vitro of these tablets was measured by the USP Paddle Method at 100 rpm in 900 ml of aqueous buffer (pH 7.2). Results are shown in Table 2.

TABLE 2

| In vitro Dissolution of Naproxen Tablets | |
|---|---|
| Time (Hours) | % (by wt) Released |
| 1 | 22.3 |
| 2 | 49.9 |
| 3 | 74.4 |
| 4 | 91.1 |
| 5 | 95.9 |

EXAMPLE 9

Naproxen (50 gm), lactose (11.25 gm), polydextrose (0.75 gm) and povidone (2.0 gm) were wet granulated and the granules were sieved through a 16 mesh screen. The granules were dried in a FBD at 60° C. Talc (1.2 gm) and magnesium stearate (0.6 gm) were mixed with the granules. The granules were compressed to give 100 tablets cores each containing;

| | mg/tablet |
|---|---|
| Naproxen | 500 |
| Lactose monohydrate | 112.5 |
| Polydextrose | 7.5 |
| Povidone | 20 |
| Talc | 12 |
| Magnesium stearate | 6 |

The tablet cores were then coated with an aqueous formulation (100 ml) containing polyvinylacetate phthalate (15 gm) and 0.88 ammonia solution (0.18 ml) until the cores were coated with about 20 mg (dry weight) of coat.

The in-vitro dissolution rate of these tablets was measured by placing the tablets in 0.1N hydrochloric acid for 2 hours and thereafter continuing the USP Paddle Method at 100 rpm in 900 ml of aqueous buffer pH 7.2. Results are shown in Table 3.

TABLE 3

| In vitro Dissolution of Naproxen Tablets | | |
|---|---|---|
| Time (Hours) | Medium | % (by wt) Released |
| 1 | 0.1 N Hydrochloric Acid | 0 |
| 2 | 0.1 N Hydrochloric Acid | 0 |
| 3 | pH 7.2 Buffer | 12.5 |
| 4 | pH 7.2 Buffer | 28.3 |
| 5 | pH 7.2 Buffer | 43.4 |
| 6 | pH 7.2 Buffer | 60.3 |
| 7 | pH 7.2 Buffer | 71.9 |
| 8 | pH 7.2 Buffer | 78.6 |
| 10 | pH 7.2 Buffer | 85.3 |
| 12 | pH 7.2 Buffer | 88.1 |
| 14 | pH 7.2 Buffer | 92.1 |

EXAMPLE 10

A complex of indomethacin and beta-cyclodextrin was prepared as described in GB 2016499A, Example 1.

The indomethacin complex (360 gm), lactose (20 gm) and dicalcium phosphate (62 gm) were wet granulated and the granules were sieved through a 16 mesh screen. The granules were then dried in a FBD at 60° C.

To the warmed indomethacin containing granules was added molten cetostearyl alcohol (80 gm). This mixture was allowed to air cool and then passed through a 16 mesh screen. Talc (2.0 gm) and magnesium stearate (1.0 gm) were then mixed with the graules. The granules were then compressed to give 100 tablets each containing;

| | mg/tablet | |
|---|---|---|
| Indomethacin complex | 360.0 | (equivalent to 50 mg indomethacin) |
| Lactose, anhydrous | 20.0 | |
| Dicalcium phosphate | 62.0 | |
| Cetostearyl alcohol | 80.0 | |
| Talc | 2.0 | |
| Magnesium stearate | 1.0 | |

EXAMPLES 11–13

Examples 2, 4 and 6 were repeated except that heptakis(2,6-di-O-methyl)-beta-cyclodextrin replaced polydextrose.

EXAMPLES 14–16

Examples 7, 8 and 9 were repeated except that beta-cyclodextrin replaced polydextrose.

EXAMPLE 17

Polydextrose (28 gm) was mixed with a mixture of molten cetostearyl alcohol (6 gm) and polyethylene glycol 4000 (6 gm). The granules were allowed to cool and sieved through a 20 mesh screen.

Theophylline (40 gm) was granulated with a solution of povidone (1.2 gm) in water. The granules were sieved through a 12 mesh screen and dried in a fluid bed drier. The granules were then sieved through a 20 mesh screen.

The theophylline granules and the polydextrose/wax granules were dry mixed with purified talc (0.6 gm). Prior to compression, magnesium stearate (0.6 gm) and purified talc (0.6 gm) were mixed with the granules. This mixture was then compressed to give 100 tablets each containing,

| | mg/Tablet |
|---|---|
| Theophylline | 400 |
| Povidone | 12 |
| Polydextrose | 280 |
| Cetostearyl Alcohol | 60 |
| Polyethylene Glycol 4000 | 60 |
| Purified Talc | 12 |
| Magnesium Stearate | 6 |

The in-vitro dissolution rate of these tablets was measured by the USP Paddle Method at 100 rpm in 900 ml of aqueous buffer (pH 6.5). Results are shown in TABLE 4.

TABLE 4

| In Vitro Dissolution of Theophylline Tablets | |
|---|---|
| Time (Hours) | % (by wt) Released |
| 1 | 10.3 |
| 2 | 15.3 |
| 4 | 22.8 |
| 8 | 33.9 |
| 12 | 42.3 |
| 16 | 48.4 |
| 24 | 61.4 |

EXAMPLE 18

The procedure of Example 17 was followed except that the amounts used were chosen such that each tablet contained,

| | mg/tablet |
|---|---|
| Theophylline | 400 |
| Povidone | 12 |
| Polydextrose | 140 |
| Cetostearyl Alcohol | 30 |
| Polyethylene Glycol 4000 | 30 |
| Purified Talc | 9 |
| Magnesium Stearate | 4.5 |

The in-vitro dissolution rate of these tablets was measured as described in Example 17. Results are given in TABLE 5.

TABLE 5

| In Vitro Dissolution of Theophylline Tablets | |
|---|---|
| Time (Hours) | % (by wt) Released |
| 1 | 10.9 |
| 2 | 16.4 |
| 4 | 24.5 |
| 8 | 35.6 |
| 12 | 45.5 |
| 16 | 54.5 |
| 24 | 72.2 |

EXAMPLE 19

The procedure of Example 17 was followed except that the amounts used were chosen such that each tablet contained,

| | mg/Tablet |
|---|---|
| Theophylline | 400 |
| Povidone | 12 |
| Polydextrose | 93.3 |
| Cetostearyl Alcohol | 20 |
| Polyethylene Glycol 4000 | 20 |
| Purified Talc | 8 |
| Magnesium Stearate | 4 |

The in-vitro dissolution rate of these tablets was measured as described in Example 17. Results are given in TABLE 6.

TABLE 6

| In Vitro Dissolution of Theophylline Tablets | |
|---|---|
| Time (Hours) | % (by wt) Released |
| 1 | 12.4 |
| 2 | 19.2 |
| 4 | 29.5 |
| 8 | 44.8 |
| 12 | 56.5 |
| 16 | 68.6 |

TABLE 6-continued

| In Vitro Dissolution of Theophylline Tablets | |
|---|---|
| Time (Hours) | % (by wt) Released |
| 24 | 91.9 |

EXAMPLE 20

The procedure of Example 17 was followed except that the amounts used were chosen such that each tablet contained,

| | mg/Tablet |
|---|---|
| Theophylline | 400 |
| Povidone | 12 |
| Polydextrose | 70 |
| Cetostearyl Alcohol | 15 |
| Polyethylene Glycol 4000 | 15 |
| Purified Talc | 7.8 |
| Magnesium Stearate | 3.7 |

The in-vitro dissolution rate of these tablets was measured as described in Example 17. Results are given in TABLE 7.

TABLE 7

| In Vitro Dissolution of Theophylline Tablets | |
|---|---|
| Time (Hours) | % (by wt) Released |
| 1 | 12.7 |
| 2 | 19.6 |
| 4 | 30.9 |
| 8 | 48.6 |
| 12 | 66.5 |
| 16 | 80.8 |
| 24 | 94.5 |

EXAMPLE 21

Theophylline (40 gm) and polydextrose (21.8 gm) were mixed and granulated with water. The granules were dried in a fluid bed drier. The dried granules were sieved through a 16 mesh screen. The dried granules were mixed with a molten (70° C.) mixture of PEG 6000 (2.9 gm) and lauryl alcohol (2.9 gm). The "waxed" granules were then cooled, before blending with talc (1.0 gm) and magnesium stearate (0.4 gm). Compression of the granules gave 100 tablets each containing,

| | mg/Tablet |
|---|---|
| Theophylline | 400 |
| Polydextrose | 218 |
| Polyethylene Glycol 6000 | 29 |
| Lauryl Alcohol | 29 |
| Purified Talc | 10 |
| Magnesium Stearate | 4 |

EXAMPLES 22-25

The procedure of Example 21 was followed except that the lauryl alcohol was then replaced by, respectively, myristyl alcohol, cetyl alcohol, stearyl alcohol and cetostearyl alcohol.

EXAMPLE 26

Polydextrose (12.6 gm) was mixed with molten cetostearyl alcohol (5.4 gm). The granules were allowed to cool and sieved through a 20 mesh screen.

Metoclopramide HCl (3.0 gm) was dry mixed with the polydextrose/alcohol granules and purified talc (0.21 gm). Prior to compression, magnesium stearate (0.21 gm) and purified talc (0.21 gm) were mixed with the granules. This mixture was then compressed to give 100 tablets each containing,

|  | mg/Tablet |
| --- | --- |
| Metoclopramide HCl | 30 |
| Polydextrose | 126 |
| Cetostearyl Alcohol | 54 |
| Purified Talc | 4.2 |
| Magnesium Stearate | 2.1 |

EXAMPLE 27

The procedure of Example 26 was followed except that the amounts used were chosen such that each tablet contained,

|  | mg/Tablet |
| --- | --- |
| Metoclopramide HCl | 30 |
| Polydextrose | 210 |
| Cetostearyl Alcohol | 90 |
| Purified Talc | 6.6 |
| Magnesium Stearate | 3.3 |

EXAMPLE 28

The procedure of Example 26 was followed except that the amounts used were chosen such that each tablet contained,

|  | mg/Tablet |
| --- | --- |
| Metoclopramide HCl | 30 |
| Polydextrose | 420 |
| Cetostearyl Alcohol | 180 |
| Purified Talc | 12.6 |
| Magnesium Stearate | 6.3 |

EXAMPLE 29

Salbutamol sulphate (0.964 gm), equivalent to 0.8 gm base salbutamol was wet granulated with anhydrous lactose (20.8 gm), polydextrose (1.25 gm) and povidone (0.3 gm) and the granules were sieved through a 16 mesh screen. The granules were then dried in a FBD at 60° C.

To the warmed salbutamol containing granules was added molten cetostearyl alcohol (5.5 gm). The mixture was allowed to air cool and then passed through a 16 mesh screen.

Talc (0.8 gm) and magnesium stearate (0.4 gm) were mixed with the granules. The granules were then compressed to give 100 tablets each containing,

| Salbutamol Sulphate | 9.64 |
| --- | --- |
| Lactose, anhydrous | 208 |
| Polydextrose | 12.5 |
| Povidone (K30) | 3 |
| Cetostearyl Alcohol | 55 |
| Talc | 8 |
| Magnesium Stearate | 4 |

The in-vitro dissolution rate of these tablets was measured by the USP Paddle Method at 100 rpm in 900 ml of aqueous buffer (pH 6.5). Results are given in TABLE 8.

TABLE 8

| In Vitro Dissolution of Salbutamol Tablets ||
| --- | --- |
| Time (Hours) | % (by wt) Released |
| 1 | 49.5 |
| 2 | 62.4 |
| 3 | 73.2 |
| 4 | 79.1 |
| 5 | 85.5 |
| 6 | 91.0 |

EXAMPLE 30

The procedure of Example 29 was followed except that the amounts used were chosen such that each tablet contained,

|  | mg/tablet |
| --- | --- |
| Salbutamol Sulphate | 9.64 |
| Lactose, anhydrous | 190.36 |
| Polydextrose | 30 |
| Povidone (K30) | 3 |
| Polydextrose | 30 |
| Povidone (K30) | 3 |
| Cetostearyl Alcohol | 55 |
| Talc | 8 |
| Magnesium Stearate | 4 |

The in-vitro dissolution rate of the tablets was measured as described in Example 29. Results are given in TABLE 9.

TABLE 9

| In Vitro Dissolution of Salbutamol Tablets ||
| --- | --- |
| Time (Hours) | % (by wt) Released |
| 1 | 43.8 |
| 2 | 61.1 |
| 3 | 71.4 |
| 4 | 77.9 |
| 5 | 80.9 |
| 6 | 82.3 |

EXAMPLE 31

The procedure of Example 29 was followed except that the amounts used were chosen such that each tablet contained,

|  | mg/Tablet |
| --- | --- |
| Salbutamol Sulphate | 9.64 |
| Lactose, anhydrous | 160.36 |
| Polydextrose | 60 |
| Povidone | 3 |
| Cetostearyl Alcohol | 55 |
| Talc | 8 |
| Magnesium Stearate | 4 |

(pH 6.5). Results are given in TABLE 10.

TABLE 10

| In Vitro Dissolution of Salbutamol Tablets ||
| --- | --- |
| Time (Hours) | % (by wt) Released |
| 1 | 41.0 |
| 2 | 57.8 |
| 3 | 68.0 |
| 4 | 74.6 |
| 5 | 81.0 |

TABLE 10-continued

| In Vitro Dissolution of Salbutamol Tablets | |
|---|---|
| Time (Hours) | % (by wt) Released |
| 6 | 83.1 |

EXAMPLE 32

Quinidine polygalacturonate (41.25 gm), lactose (4.5 gm), hydroxypropylmethyl cellulose (1.25 gm) and polydextrose (4.5 gm) were granulated with water. The granules were sieved through a 16 mesh screen and dried in a fluid bed drier. The granules were mixed with molten cetostearyl alcohol (9.0 gm) and allowed to cool. The granules were sieved through a 16 mesh screen and blended with purified talc (1.0 gm). The granules were compressed to give 100 tablets each containing,

| | mg/Tablet |
|---|---|
| Quinidine Polygalacturonate | 412.5 |
| Lactose | 45 |
| Hydroxypropylmethyl cellulose | 12.5 |
| Polydextrose | 45 |
| Cetostearyl Alcohol | 90 |
| Purified Talc | 10 |

The in-vitro dissolution rate of these tablets was measured by the USP Paddle Method at 100 rpm in 900 ml of buffer (pH 6.5).

The in-vitro dissolution rate of these tablets was measured by the USP Paddle Method at 100 rpm in 900 ml of buffer (pH 6.5). Results are given in TABLE 11.

TABLE 11

| In Vitro Dissolution of Quinidine Tablets | |
|---|---|
| Time (Hours) | % (by wt) Released |
| 1 | 15.2 |
| 2 | 26.0 |
| 4 | 41.5 |
| 8 | 60.1 |
| 12 | 72.5 |
| 16 | 79.9 |
| 20 | 89.9 |

CLINICAL STUDIES

A pharmacokinetic study in 3 healthy volunteers was performed on tablets prepared as described in Example 7. Samples were analysed by enzyme immunoassay. Mean plasma theophylline concentrations are given in TABLE 12.

TABLE 12

| Time (Hours) | Mean Plasma Theophylline Concentrations (ug/ml) |
|---|---|
| 0 | 0.0 |
| 1 | 0.7 |
| 2 | 1.6 |
| 3 | 2.1 |
| 4 | 2.7 |
| 7 | 3.0 |
| 8 | 3.0 |
| 10 | 2.5 |
| 12 | 2.1 |
| 24 | 1.4 |

It can therefore be seen that the composition of Example 7 exhibits excellent control over the release of theophylline in vivo.

What is claimed is:

1. A solid, controlled release pharmaceutical composition comprising a pharmaceutically active ingredient incorporated in a matrix comprising a first substance selected from the group consisting of a water soluble polydextrose, a water soluble cyclodextrin and a cellulose ether, and a second substance selected from the group consisting of a $C_{12}$–$C_{36}$ fatty alcohol and a polyalkylene glycol.

2. The composition according to claim 1 wherein the first substance is a cyclodextrin.

3. The composition according to claim 2 wherein the first substance is a beta-cyclodextrin.

4. The composition according to claim 1 wherein the fatty alcohol is a $C_{14}$–$C_{22}$ fatty alcohol.

5. The composition according to claim 1 wherein the fatty alcohol is selected from the group consisting of cetyl alcohol, stearyl alcohol, cetostearyl alcohol and myristyl alcohol.

6. The composition according to claim 1 wherein the polyalkylene glycol is polyethylene glycol.

7. The composition according to claim 1 wherein the first substance is a cellulose ether.

8. The composition according to claim 7 wherein the cellulose ether is at least one of a hydroxyalkylcellulose and a carboxyalkylcellulose.

9. The composition according to claim 1 wherein the ratio of the first substance to the second substance is between 6 to 1 and 1 to 6.

10. The composition according to claim 9 wherein the ratio is between 4 to 1 and 1 to 4.

11. The composition according to claim 1 wherein the composition contains between 1% and 80% (w/w) of the first substance.

12. The composition according to claim 11 wherein the composition contains between 1% and 50% (w/w) of the first substance.

13. The composition according to claim 12 wherein the composition contains between 2% and 40% (w/w) of the first substance.

14. The composition according to claim 1 wherein the active ingredient is a water isoluble drug.

15. A preparation in which a pharmaceutically active ingredient can be incorporated for the production of a solid, controlled release, pharmaceutical composition, said preparation comprising a matrix of a first substance selected from the group consisting of a water soluble polydextrose, a water soluble cyclodextrin and a cellulose ether, and a second substance selected from the group consisting of a $C_{12}$–$C_{36}$ fatty alcohol and a polyalkylene glycol.

16. The preparation according to claim 15 wherein the first substance is a cyclodextrin.

17. The preparation according to claim 16 wherein the first substance is a beta-cyclodextrin.

18. The preparation according to claim 15 wherein the fatty alcohol is a $C_{14}$–$C_{22}$ fatty alchol.

19. The preparation according to claim 18 wherein the fatty alcohol is selected from the group consisting of cetyl alcohol, stearyl alcohol, cetostearyl alcohol and myristyl alcohol.

20. The preparation according to claim 15 wherein the polyalkylene glycol is polyethylene glycol.

* * * * *